US005877147A

United States Patent [19]
Pinegin

[11] Patent Number: 5,877,147
[45] Date of Patent: Mar. 2, 1999

[54] COMPOUNDS FOR MEDICINAL USE

[75] Inventor: Boris Vladimirovich Pinegin, Moscow, Russian Federation

[73] Assignee: Peptech (UK) Limited, United Kingdom

[21] Appl. No.: 624,592

[22] PCT Filed: Oct. 5, 1994

[86] PCT No.: PCT/GB94/02167

§ 371 Date: Jun. 29, 1996

§ 102(e) Date: Jun. 29, 1996

[87] PCT Pub. No.: WO95/10293

PCT Pub. Date: Apr. 20, 1995

[30] Foreign Application Priority Data

Oct. 8, 1993 [GB] United Kingdom .................. 9320820

[51] Int. Cl.⁶ .................................................. A61K 38/00
[52] U.S. Cl. ................................. 514/8; 514/17; 530/322; 424/117; 260/117.5
[58] Field of Search ................................ 530/322; 514/8, 514/17; 424/117; 260/112.5

[56] References Cited

U.S. PATENT DOCUMENTS

| | | | |
|---|---|---|---|
| 4,101,536 | 7/1978 | Yamamura et al. | 260/112.5 R |
| 4,186,194 | 1/1980 | Adam et al. | 424/89 |
| 4,235,771 | 11/1980 | Adam et al. | 260/112.5 R |
| 4,317,771 | 3/1982 | Shiba et al. | 260/112.5 R |
| 4,370,265 | 1/1983 | Adam et al. | 260/122.5 R |
| 4,395,399 | 7/1983 | Ovchinnokov et al. | 424/177 |
| 4,406,890 | 9/1983 | Tarcsay et al. | 424/177 |
| 4,430,265 | 2/1984 | Yamamura et al. | 260/112.5 R |
| 4,461,761 | 7/1984 | Lefrancier et al. | 424/177 |
| 4,522,811 | 6/1985 | Eppstein et al. | 514/2 |
| 4,684,625 | 8/1987 | Eppstein et al. | 514/19 |
| 4,774,085 | 9/1988 | Fidler | 424/85.5 |
| 5,189,014 | 2/1993 | Cowan, Jr. | 514/2 |
| 5,210,072 | 5/1993 | Chedid et al. | 514/8 |

FOREIGN PATENT DOCUMENTS

| | | |
|---|---|---|
| 54-73729 | 6/1979 | Japan . |
| 55-19236 | 2/1980 | Japan . |
| WO 93/10148 | 5/1993 | WIPO . |

OTHER PUBLICATIONS

Andronova, T.M., Glucosaminylmuramyldipeptide (GMDP). Synthesis and Immunoadjuvant Activity, Chim. Oggi, 9 (12), pp. 21–25, 1991.

Mescheryakova, et al. Structure –Function Investigation of Glucoasminylmuramylpeptides, Bioorganicheskaya Khimiya, vol. 17, No. 9, pp. 1157–1165, 1991.

Ivanov, et al., Structure, Design, and Synthesis of Immunoactive Peptides, Pure & Appl. Chem., vol. 59, No. 3, pp. 317–324, 1987.

Dorland's Illustrated Medical Dictionary, 27th Edition, pp. 912–913, 1105, 1333, 1774, 1876, 1988.

Chedid et al., Potential Use of Muramyl peptides in Cancer Therapy and Prevention, Bact. Cancer, pp. 49–65, 1982.

Dozmorov, et al., Study of immunomodulatory Properties of N–Acetylmuramyl–L–Alany–D–Isoglutamine and N–Acetylglucosaminyl–(beta 1–4)–N–Acetylmuramyl–L–Alanyl–D–Isoglutamine, Biomed. Sci., pp. 651–658, 1991.

Azuma, Ichiro, Immunological Properties of Muramyl Dipeptides (MDP) and Related Synthetic Compounds, Kekkaku, 67(9), pp. 637–642, 1992.

Azuma, et al., Stimulation With Synthetic acyl–MDP Derivatives of Host–Defense Mechanism Against Cancer and Viral Infections, Nat. Immun., Cancer, Biol. Response Modif., 1st (1986), Meeting Date 1985, 1986.

Acevedo, et al., Prevention of Oncogenic Viral Infections in Mice with CGP 11637, a Synthetic Muramyl Dipeptide Analog, Antimicrob. Agents Chemother., 28(5), pp. 589–596, 1985.

Gangemi, et al., Novel Approaches for Targeting Antiviral Agents in the Treatment of Arena–, Bunya, Flavi–, and Retroviral Infections, Report (1991), Order No. AD–A243598, 294 pp. 1992.

Lazdins, et al., the Lipophilic Muramyl Peptide MTP–PE is a Potent Inhibitor of HIV Replication in Macrophages, AIDS Res. Hum. Retroviruses, 6(10), pp. 1157–1161, 1990.

Masihi, et al., Muramyl Dipeptide Inhibits Replication of Human Immunodeficiency Virus In Vitro, AIDS Res. Hum. Retroviruses, 6(3), pp. 393–399, 1990.

Masihi, et al., Muramyl Peptides Confer Hepatoprotection Against Murine Viral Hepatitis, Int. J. Immunopharmacol., 11(8), pp. 879–886, 1989.

Iida, et al., Prophylactic Activity Against Sendai Virus Infection and Macrophage Activation with Lipophilic Derivatives of N–acetylglucosaminylmuramyl Tri– or Tetrapeptides, Vaccine, 7(3), pp. 225–228, 1989.

Chomel, et al., Prophylactic aand Terapeutic Effects of Murabutide in OF1 Mice Infected with Influenze A/H3N2 (A/Texas/1/77) Virus, J. Biol. Respons. Modif., 7(6), pp. 581–586, 1988.

Dietrich, et al., Enhancement of Host Resistance Agaisnt Virus Infections by MTP–PE, a Synthetic Lipophilic Muramyl Peptide, Int. J. Immunopharmacol. 8(8), pp. 931–942, 1986.

Phillips, et al., Modulation of Murine Lymphoma Growth by MDP, MDP(D–D) and Cyclophosphamide, Int. J. Immunopharmacol., 5(3), pp. 219–227, 1983.

Fidler, I.J., "Optimization and Limitations of Systemic Treatment of Murine Melanoma Metastases with Liposomes Containing Muramyl Tripeptide Phosphatidylethanolamine," Cancer Immunol. Immunother. 21:169–173 (1986).

(List continued on next page.)

Primary Examiner—Cecilia J. Tsang
Assistant Examiner—Bennett Celsa
Attorney, Agent, or Firm—Sterne, Kessler, Goldstein & Fox P.L.L.C.

[57] ABSTRACT

Muramyl peptide compounds are useful in the prophylaxis of cancers and particularly in the treatment of precancerous lesions associated with cancers of the mucosa or epithelium.

19 Claims, 2 Drawing Sheets

OTHER PUBLICATIONS

Fidler, I.J., et al., "Systemic Activation of Tumoricidal Properties in Mouse Macrophages and Inhibition of Melanoma Metastases by the Oral Administration of MTP–PE, a Lipophilic Muramyl Dipeptide," *J. Immunol.* 138(12):4509–4514 (1987).

Key, M.E., et al., "Isolation of Tumoricidal Macrophages From Lung Melanoma Metastases of Mice Treated Systemically With Liposomes Containing a Lipophilic Derivative of Muramyl Dipeptide," *J. Nat. Canc. Inst.* 69(5):1189–1198 (1982).

Kiso, M., et al., "Synthesis and Immunoadjuvant Activities of Novel N–acylmuramoyl Dipeptides Related to the Lipid A Constituent of the Bacterial Lipopolysaccharide," *Carbohydrate Res.* 90:C8–C11 (1981).

Kiso, M., et al., "Biological Activities of Fundamental, Carbohydrate Skeleton of Lipid A Containing Amide–linked 3–Hydroxytetradecanoic Acid," *Agric. Biol. Chem.* 45(6):1523–1525 (1981).

Kleinerman, E.S., et al., "Influence of Chemotherapy Administration on Monocyte Activation by Lispsomal Muramyl Tripeptide Phosphatidylethanolamine in Children With Osteosarcoma," *J. Clin. Oncol.* 9(2):259–267 (1991).

Kleinerman, E.S., et al., "Unique Histological Changes in Lung Metastases of Osteosarcoma Patients Following Therapy with Liposomal Muramyl Tripeptide (CGP 19835A Lipid)," *Cancer Immunol. Immunother.* 34:211–220 (1992).

Kotani, S., et al., "Immunobiological Activities of Synthetic Lipid A Analogs with Low Endotoxicity," *Infect. Immun.* 54(3):673–682 (1986).

Maeda, H., et al., "Adjuvant Activities of Synthetic Lipid A Subunit Analogues and its Conjugates with Muramyl Dipeptide Derivatives," *Vaccine* 7(3):275–281 (1989).

Phillips, N.C., et al., "Induction of Murine Macrophage Tumoricidal Activity and Treatment of Experimental Pulmonary Metastases by Liposomes Containing Lipophilic Muramyl Dipeptide Analogs," *J. Biol. Modif.* 6:678–691 (1987).

English language abstract for Japanese patent document JP 54–73729 (Doc. Ref. AL1), Derwent WPI Accession No. 79–55076B/30.

English language abstract for Japanese patent document JP 55–19236 (Doc. Ref. AM1), Derwent WPI Accession No. 80–21241C/12.

*—COMPARISON OF NON-INFECTED CONTROL GROUP WITH PATIENT GROUP, PRE-THERAPY ($p<0.01$)

**—COMPARISON OF PATIENT GROUPS BEFORE AND AFTER TREATMENT ($p<0.01$)

FIG.1

*—COMPARISON OF NON-INFECTED CONTROL GROUP WITH PATIENT GROUP, PRE-THERAPY ($p<0.01$)

**—COMPARISON OF PATIENT GROUPS BEFORE AND AFTER TREATMENT ($p<0.01$)

COMPOUNDS FOR MEDICINAL USE

FIELD OF THE INVENTION

The present invention relates to the use of muramyl peptide compounds in the prophylaxis of cancers, including the treatment of pre-cancerous conditions.

BACKGROUND OF THE INVENTION

Cancer is a term which is used to describe the development of abnormal cells which grow in a rapid and uncontrolled manner and are often invasive. The invasion of vital organs frequently results in the death of a patient.

Cancer is extremely widespread and, indeed, it is thought that about 30% of people are likely to contract cancer at some time in their lives with cancer being the cause of death in around 20%. Traditional treatments for cancer include surgery and radiotherapy but, more recently, attention has been turned to the development of chemotherapeutic or cytotoxic agents which can damage or kill cancer cells.

In recent years, increasing attention has been drawn towards the occurrence of tissue changes that are indicative of an increased risk for the subsequent development of particular cancers at that site of change. A variety of these have been described, including modifications of the intestinal wall (intestinal polyps) which are associated with increased incidence of cancers of the colon and rectum, alterations of the skin (actinic keratoses) which are associated with carcinomas of the skin, and condylomata of the cervix, which are associated with cancer of the uterine cervix. To one skilled in the art, these conditions or tissue changes tending to proceed to cancer, to be associated with the development of cancer, or to carry a significant risk of cancer are known as precancerous conditions or lesions. In some cases, the cause of these precancerous conditions is reasonably well established, as in the case of actinic keratoses resulting from excessive exposure to sunlight, or infection with human papilloma virus in the case of condylomata of the cervix (Cancer in Practice by G J G Rees, S E Goodman and J A Bullimore. Pub Butterworth-Heinemann, Oxford, 1993). In other cases, the cause of the precancerous lesion has not been identified.

The present invention relates to the use of certain muramyl peptide compounds (MDPs) in the prophylaxis of cancer and especially in the treatment of precancerous lesions.

It has long been known that non-specific stimulation of the immune system can be brought about by exposure to bacteria, or components extracted from bacterial cells. The specific components responsible for this activity were identified as sugar-containing peptides of the cell wall, and further biochemical analysis of the peptides identified them as the peptidoglycan component of the cell wall. The smallest effective synthetic molecule was found to be an N-acetyl-muramyl-L-alanyl-D-isoglutamine (Merser et al, *Biochem. Biophys. Res. Comm.* 66 1316 (1975)) which is often referred to as a prototype muramyl dipeptide or prototype MDP.

Subsequently, a wide variety of analogues of prototype muramyl dipeptide were synthesised, some of which have been proposed as treatments for the restoration of immune function or the non-specific stimulation of the immune system. These analogues, and prototype MDP itself are known as muramyl peptide compounds (MDPs).

In the past, some work has been carried out on the use of MDPs in the treatment of cancer and, for example, Key et al, *J. Natl. Cancer Inst.*, 69(5), 1189–1198 (1982) describe the treatment of lung melanoma metastases with liposomes containing an MDP derivative. Later, the same group of workers investigated the optimal conditions and limitations for the eradication of melanoma metastases using a liposome encapsulated MDP derivative, MTP-PE (Fidler et al, *Cancer Immunol. Immunother.*, 21(3) 169–173 (1986)). In addition it was found that orally administered non-liposome encapsulated MTP-PE produced tumouricidal activity in both lung and peritoneal macrophages and was effective in inhibiting lung and lymph node metastasis although it was not effective in eradicating well established melanoma metastases (Fidler et al, *J. Immunol.*, 138(12), 4509–4514 (1987)).

Phillips et al, *J. Biol. Response Modif.*, 6(6), 678–691 also describe work relating to the treatment of experimental pulmonary metastases using liposomes containing lipophilic MDP analogues. Again, the compounds were used to treat experimentally induced pulmonary B16 melanoma tumours in mice. However, Kleinerman et al in *J. Clin. Oncology*, 9(2), 259–267 (1991) concluded that it is unlikely that the MDP derivative L-MTP-PE can serve as a single modality in treating metastatic disease.

Some MDPs have been used in clinical trials for human therapy. For example, Kleinerman et al (Kleinerman, E S, *Cancer Immunol. Immunother*, 34: 211–220, 1992) have used a lipophilic analogue in a liposomal formulation in the treatment of lung metastases developed in patients with osteosarcoma.

SUMMARY OF THE INVENTION

Despite the above attempts to demonstrate the utility of MDPs in the treatment of cancer, and despite the fact that MDP was discovered about 20 years ago, no single example of a significant beneficial effect of MDP in the treatment of a cancer in man has been recorded.

However, the present inventors have now discovered that certain muramyl peptide derivatives are particularly effective in a method for the treatment of precancerous lesions, the method comprising administering to a patient suffering from a precancerous lesion an effective amount of a muramyl peptide compound. This method of treatment therefore constitutes a prophylactic approach to the treatment of cancers.

Not only is this approach novel, it is clearly beneficial to the patient, as it is always preferable to prevent the occurrence of a cancer rather than undergo the long, dangerous, uncomfortable and frequently unsuccessful treatment of an existing cancer.

Therefore, in a first aspect of the present invention, there is provided the use of a muramyl peptide compound in the preparation of an agent for the treatment of a precancerous lesion.

The agent may be used for the treatment of any type of precancerous lesion although it is especially preferred for the treatment of precancerous lesions leading to mucosal or epithelial cancers.

The present invention also provides the use of a muramyl peptide compound in the preparation of an agent for the prophylaxis of a cancer.

Again, the agent may be used for the prophylaxis of any type of cancer although it is most succesfully used for the prophylaxis of epithelial and mucosal originating cancers. The prophylactic activity of the agent arises in some cases from its use in the treatment of precancerous lesions but there may also be cases where the agent has a prophylactic effect for patients at risk of cancer but having no precancerous lesions.

Pyrogenicity is a problem which has caused difficulties for the exploitation of certain muramyl peptide compounds. Pyrogenicity may be attenuated by appropriate formulations (for example the liposomal formulations of U.S. Pat. No. 4,522,811 and U.S. Pat. No. 4,684,625), but in general it will be preferable to choose for use in the present invention a muramyl peptide compound of low intrinsic pyrogenicity.

DETAILED DESCRIPTION OF THE INVENTION

Many muramyl peptide compounds useful in the present invention fall within general formula I:

wherein:
- $R^1$ represents a hydrogen atom or a $C_1$–$C_{22}$ acyl group;
- $R^2$ represents a hydrogen atom or a $C_1$–$C_{22}$ acyl group;
- $R^3$ represents a hydrogen atom or a $C_1$–$C_6$ alkyl group;
- $R^4$ represents a $C_1$–$C_{21}$ alkyl group or a $C_6$ or $C_{10}$ aryl group;
- $R^5$ represents a hydrogen atom; and
- R represents the residue of an amino acid or a linear peptide built up of from 2 to 6 amino acid residues, at least one of the residues being optionally substituted with a lipophilic group.

Preferred acyl groups for $R^1$ and $R^2$ are $C_1$–$C_5$ acyl groups such as acetyl; it will be appreciated that the carbon count in the acyl group does not include the carbonyl moiety. Preferred alkyl groups for $R^3$ are $C_1$–$C_4$ alkyl groups such as methyl and ethyl. Preferred alkyl groups for $R^4$ are $C_1$–$C_6$ alkyl groups, particularly $C_1$–$C_4$ alkyl groups, such as methyl or ethyl; phenyl is a preferred aryl group.

R preferably represents a mono-, di- or tri-peptide. The proximal peptide residue (or the only peptide residue, if there is only one) is preferably that of an L-amino acid. Examples include:

| | |
|---|---|
| L-alanyl | L-tryptophanyl |
| L-valyl | L-lysyl |
| L-leucyl | L-ornithyl |
| L-isoleucyl | L-arginyl |
| L-α-aminobutyryl | L-histidyl |
| L-seryl | L-glutamyl |

-continued

| | |
|---|---|
| L-threonyl | L-glutaminyl |
| L-methionyl | L-aspartyl |
| L-cysteinyl | L-asparaginyl |
| L-phenylalanyl | L-prolyl |
| L-tyrosyl | L-hydroxyprolyl |

L-alanyl is preferred, as is L-threonyl.

The next amino acid from the proximal end of the peptide is preferably of the D-configuration. It is preferably acidic and may be D-glutamic or D-aspartic acid or a mono-, di- or mixed $C_1$–$C_{22}$ (preferably $C_1$–$C_6$) alkyl ester, amide or $C_1$–$C_4$ alkyl amide thereof. (The expression "mixed" is illustrated when one carboxyl group is amidated and the other esterified. D-isoglutamine and D-glutamate are preferred.

A third amino acid residue from the proximal end of the chain, if there is one, is preferably of the L-configuration, as indicated above in relation to the proximal amino acid residue. L-alanyl and L-lysyl are preferred.

The amino acid residue or linear peptide is optionally substituted with at least one lipophilic group. The lipophilic group may be a $C_{10}$–$C_{22}$ acyl group such as stearoyl or a di-($C_{10}$–$C_{22}$ acyl)-sn-glycero-3'-hydroxy-phospheryloxy-group wherein for example each of the $C_{10}$–$C_{22}$ acyl groups can be a palmitoyl group. The lipophilic group may alternatively (or in addition, as more than one substitution may be present) be a $C_1$–$C_{10}$ester group, such as a $C_2$–$C_6$ ester group: a butyl ester is an example.

Examples of muramyl dipeptides within the scope of general formula I include:

- muroctasin, otherwise known as MDP-Lys (L18) ($N^2$-(N-acetylmuramyl-L-alanyl-D-isoglutaminyl)-$N^6$-stearoyl-L-lysine);
- MTP-PE (N-acetyl-muramyl-L-alanyl-D-isoglutaminyl-L-alanyl-2-(1',2'-dipalmitoyl-sn-glycero-3'-hydroxy-phosphoryloxy)ethylamide, monosodium);
- murabutide (N-acetylmuramyl-L-alanyl-D-glutamine-α-N-butyl ester); and
- t-MDP (N-acetylmuramyl-L-threonyl-D-isoglutamine).

The preparation of muroctasin is disclosed in EP-A-0021367 and U.S. Pat. No. 4,317,771. The preparation of MTP-PE is disclosed in EP-A-0025495. The preparation of murabutide is described in Lefrancier et al, *J. Med. Chem.*, 25 87 (1982). The preparation of t-MDP can be prepared by methods known in the art. Patent publications which give details of the preparations of muramyl peptide compounds generally include BE-A-0834753, BE-A-0834754, BE-A-0847103, BE-A-0849214, DE-A-2710455, DE-A-2922533, DE-A-2747379, DE-A-2912865, FR-A-2355505, FR-A-2358159, FR-A-2375249, EP-A-0004512, EP-A-0002677, JP-A-54063016, JP-A-54073729, JP-A-55019236, U.S. Pat. No. 4,082,735 and U.S. Pat. No. 4,082,736. (The preparation of prototype muramyl dipeptide is disclosed in DE-A-2450355 and U.S. Pat. No. 4,235,771.) All the documents referred to in this specification are incorporated herein by reference.

Not all muramyl dipeptides useful in the present invention fall within general formula I. Many fall within general formula II, which represents a very much preferred group of compounds for use in the invention:

wherein:
R represents a residue of an amino acid or a linear peptide built of from 2 to 6 amino acid residues, at least one of the residues being optionally substituted with a lipophilic group; and
n is 1 or 2.

The compound may also be an anomer of general formula II. Preferred values for R are as described above in relation to general formula I. It is particularly preferred that the peptide R correspond to the peptide in prototype MDP (L-Ala-D-isoGln). Alternatively, in another preferred embodiment, R may represent L-Ala-D-Glu.

The preferred value for n is 1.

Compounds of general formula II are disclosed in U.S. Pat. No. 4,395,399 and the preferences set out in that document are equally preferred in the present invention. Additionally, in this invention, the group R may be substituted lipophilically as described above.

One of the most preferred compounds for use in the present invention falls within general formula II and is N-acetyl-D-glucosaminyl-(β1–4)-N-acetylmuramyl-L-alanyl-D-isoglutamine (GMDP), the structure of which is:

GMDP

This compound (Compound II in U.S. Pat. No. 4,395,399), also known as glycopin, has already undergone pre-clinical toxicity testing and pharmacokinetic investigations required for licensing for clinical use in the USSR (as it then was). The acute toxicity in mice, measured by the $LD_{50}$ test is 7 g/kg. This figure shows the compound to be almost an order of magnitude less toxic than muroctasin which has an $LD_{50}$ value in mice of 625 mg/kg and for which the therapeutic use is associated with unpleasant side effects such as fever.

While the pyrogenicity of GMDP is about 50% that of MDP and has not prevented its clinical evaluation, it may in some circumstances be preferable to use an even less pyrogenic analogue. Such an analogue is available, and is N-acetyl-D-glucosaminyl-(β1–4)-N-acetylmuramyl-L-alanyl-D-glutamic acid (GMDP-A), which is Compound III in U.S. Pat. No. 4,395,399, and whose structure is as follows:

GMDP-A

Other preferred compounds within the scope of general formula II include:

N-acetyl-D-glucosaminyl-(β1–4)-N acetylmuramyl-L-alanyl-L-isoglutamine (GMDP-LL) which has the structure:

GMDP-LL

N-acetyl-D-glucosaminyl-(β1–4)-N acetylmuramyl-L-alanyl-D-glutamine n-butyl ester (GMDP-OBu) which has the structure:

GMDP-OBu

N-acetyl-D-glucosaminyl-(β1–4)-N acetylmuramyl-L-alanyl-D-isoglutaminyl-L-lysine (GMDP-Lys) which has the structure:

GMDP-Lys

$N^\alpha$-[N-acetyl-D-glucosaminyl-($\beta$1–4)-N-acetylmuramyl-L-alanyl-D-isoglutaminyl]-$N^\epsilon$-stearoyl-L-lysine (GMDP-Lys(St)) which has the structure:

GMDP-Lys(St)

Other useful compounds include:

$N^\alpha$-[N-Acetyl-D-glucosaminyl-($\beta$1–4)-N-acetyl-muramyl-L-alanyl-$\gamma$-D-glutamyl]-$N^\epsilon$-stearoyl-L-lysine which has the structure:

GMDPA-Lys(St)

N-Acetyl-D-glucosaminyl-($\beta$1–4)-N-acetylmuramyl-L-alanyl-D-glutamic acid dibenzyl ester which has the structure:

GMDPA(OBzl)$_2$

N-Acetyl-D-glucosaminyl-($\beta$1–4)-N-acetylmuramyl-N-methyl-L-alanyl-D-isoglutamine which as the structure:

Me-GMDP

N-Acetyl-D-glucosaminyl-($\beta$1–4)-N-acetylmuramyl-($\beta$1–4)-N-acetyl-D-glucosaminyl-($\beta$1–4)-N-acetylmuramyl-bis-(L-alanyl-D-isoglutamine) which has the structure:

(GMDP)₂

N-Acetyl-D-glucosaminyl-(β1–4)-N-acetylmuramyl-(β1–4)-N-acetyl-D-glucosaminyl-(β1–4)-N-acetylmuramyl-bis-(L-alanyl-D-glutamic acid) which has the structure:

(GMDPA)₂

N-Acetyl-D-glucosaminyl-(β1–4)-N-acetylmuramyl-(β1–4)-N-acetyl-D-glucosaminyl-(β1–4)-N-acetylmuramyl-bis-(L-alanyl-D-isoglutaminyl-L-lysine) which has the structure:

(GMDP Lys)₂

N-acetyl-D-glucosaminyl-(β1–4)-N-acetylmuramyl-(β1–4)-N-acetyl-D-glucosaminyl-(β1–4)-N-acetylmuramyl-bis-[L alanyl-D-isoglutaminyl-N$^\epsilon$-stearoyl-L-lysine]:

[GMDP-Lys(St)]₂

N-Acetyl-D-glucosaminyl-(β1–4)-N-acetylmuramyl-L-alanyl-D-isoglutamine 1-adamantyl ester which has the structure:

GMDP-Ad

L-Threonyl-N$^\epsilon$- [N-Acetyl-D-glucosaminyl-(β1–4)-N-acetyl-muramyl-L-alanyl-γ-D-isoglutaminyl]-L-lysyl-L-prolyl-L-arginine which has the structure:

GMDP-tuftsin E

N-Acetyl-D-glucosaminyl-(β1–4)-N-acetyl-muramyl-L-alanyl-γ-D-isoglutaminyl-L-threonyl-L-lysyl-L-prolyl-L-arginine which has the structure:

GMDP-tuftsin A

N-Acetyl-D-glucosaminyl-(β1–4)-N-acetylmuramyl-L-alanyl-α-D-glutamyl-L-lysyl-L-threonyl-N^ε-stearoyl-L-lysyl-L-prolyl-L-arginine which has the structure:

GMDPA-tuftsin lipophilic $N^\epsilon$-[N-Acetyl-D-glucosaminyl-(β1–4)-N-acetyl-muramyl-L-alanyl-γ-D-isoglutaminyl]-L-lysyl-L-histidyl-L-glycine amide which has the structure:

GMDPA-bursin

N-Acetyl-D-glucosaminyl-(β1–4)-N-acetylmuramyl-L-alanyl-D-isoglutaminyl-L-glutamyl-L-tryptophan which has the structure:

GMDP-thymogen I

N-Acetyl-D-glucosaminyl-(β1–4)-N-acetylmuramyl-L-alanyl-D-isoglutaminyl-ε-aminohexanoyl-L-glutamyl-L-tryptophan which has the structure:

GMDP-thymogen II $N^\alpha$-[N-Acetyl-D-glucosaminyl-(β1–4)-N-acetyl-muramyl-L-alanyl-D-isoglutaminyl]-$N^\epsilon$-stearoyl-L-lysyl-L-glutamyl-L-tryptophan which has the structure:

GMDP-thymogen III

Thr-MDP

N-acetylmuramyl-L-alanyl-D-glutamine n-butyl ester which has the structure:

Murabutide

In the above structures, the following abbreviations are used:
Bzl—benzyl;
Me—methyl;
Ahx—ε-aminohexanoyl.

The most preferred compound is GMDP followed by GMDP-A, and murabutide.

Glucosaminyl-muramyl dipeptides within the scope of general formula II can be prepared relatively cheaply and in reasonably large quantities by the process disclosed in U.S. Pat. No. 4,395,399. The preparation disclosed is based on the extraction and purification of the disaccharide component from the bacterium *Micrococcus lysodecticus* and its subsequent chemical linkage to a dipeptide synthesised for example by conventional peptide chemistry. However, the disaccharide may equally well be chemically synthesised using standard sugar chemistry.

A further advantage of the preferred compounds of general formulae I and II mentioned above is that they are water soluble which facilitates their administration to patients.

The prophylactic use of MDPs may arise from the effectiveness of the compounds in the treatment of pre-cancerous conditions.

An example of such a pre-cancerous condition occurs in cervical cancer where cancer tends to be initiated by the formation of papillomas which may be associated with infection by a strain of human papilloma virus. Papillomas can easily be detected and are generally treated by cauterisation or with liquid nitrogen followed by surgical removal. However, if left untreated, the papillomas tend to progress to neoplasia and the formation of cervical cancer which is extremely difficult to treat. Since the mortality rate of women with cervical cancer is very high, it is obviously desirable to prevent neoplasia. Prophylactic treatment of papillomas has had some measure of success, but surgical treatment does not entirely prevent recurrence. There is good evidence that colorectal cancer, mostly adenocarcinomas arising from the surface epithelium, is another type of cancer that can arise from benign precancerous lesions, in this case intestinal polyps.

Examples of other precancerous lesions (and, in parentheses, the potential subsequent malignant condition) which can be treated according to this invention are genital warts (cancer of the uterine cervix); anal warts (cancer of the anus); intestinal polyps (colorectal cancer); actinic keratoses (basal, squamous cell carcinomas and melanomas); erythroplasia of Queyrat (penile squamous carcinoma); Bowens disease (penile squamous carcinoma); penile warts (cancer of the penis); leucoplakia (cancer of the vulva); lichen planus (cancer of the oral mucosa); adenomatous gastric polyps (gastric cancer); papillomas of the bladder epithelium (bladder carcinoma); and oesophogeal papillomas (oesophageal squamous cell carcinoma).

This list is, however, given by way of example only and it should be understood that the present invention is of use in the treatment of any precancerous lesion likely to give rise to a mucosal or epithelial cancer.

In all such types of cancer, it is generally more effective to treat the pre-cancerous stage before neoplasia than to attempt to treat the cancer after neoplasia has occurred.

It will be remarked that the examples given above are all cancers of epithelial or mucosal tissue. Indeed, it is believed that the effectiveness of MDPs in the treatment of mucosal and epithelial originating cancers may arise, at least in part, from their activity as stimulators of mucosal immunity. In particular, it has been found that levels of IgA are especially high in patients treated with GMDP and GMDP-A although it should be stressed that the effectiveness of the present invention is not dependent on the correctness of this theory.

It is expected that MDPs will be especially useful in the preparation of agents for the treatment of papillomas of the cervix, anus or colorectal area, or precancerous conditions of the skin or oral mucosa. These agents will therefore be useful for the prophylaxis of the cancers just mentioned.

In some cases the treatment of the pre-cancerous condition with MDPs will result in disappearance of the precancerous condition but it may be that the treatment will simply prevent neoplasia.

In some cases, treatment of the precancerous condition will be with the MDP analogue alone. However, at other times, the treatment with the MDP analogue will be adjunct or adjuvant therapy, being performed in addition to surgery, cryosurgery, laser vaporisation, chemotherapy, immunotherapy or radiation therapy.

The observation that MDPs are effective in the treatment of pre-cancerous conditions is particularly surprising in the view of the large amount of work that has been carried out on the use of MDPs in cancer without this previously becoming apparent.

The types of cancer to which this aspect of the invention applies in particular are as mentioned above.

In certain circumstances, cancers may not be associated with detectable precancerous lesions as such. However, it is recognised in medicine that various endogenous markers exist, most of which are genetic markers, which indicate a predisposition of their carriers to particular types of cancer.

MDPs may therefore be administered to the carriers of such markers and also to other patients known to be at high risk of contracting cancer as a prophylactic treatment to prevent cancer developing. Examples of patients with a high risk of contracting cancer include patients carrying a genetic marker, patients who have a family history of the disease or people who work in a high risk environment, for example in an area which has high radiation levels.

Therefore in a further aspect of the invention there is provided the use of a muramyl peptide in the preparation of an agent for the prophylaxis of cancer in a patient carrying an endogenous marker for cancer or otherwise identified as being at high risk of contracting a cancerous condition.

This type of prophylactic use could not be contemplated with conventional cancer therapies. Radiation therapy and chemotherapy both have side effects which are much too severe to be tolerated by a healthy person who is merely at some risk of becoming ill.

The route of administration of the compounds will, of course, depend on the type of precancerous lesion or cancer being treated. However, typical routes of administration would be oral (suitable for any precancerous lesions or cancers but particularly for precancerous lesions and cancers of the mouth and GI tract); vaginal (for cervical cancer and associated precancerous lesions); rectal (for cancers and precancerous lesions of the lower GI tract, particularly colorectal cancer and the anus); and topical or transdermal (for cancers and precancerous lesions of the skin and the oral mucosa). Although the above are preferred routes of administration, it is also possible to administer the compounds parenterally, for example by intravenous or intramuscular injection. Moreover, the compounds can be instilled by catheter or other device into the locality of the tumour as, for example, papillomas of the bladder, or into the vagina and uterus for cervical cancer.

Oral formulations may be in the form of tablets, capsules or emulsions depending on the site of the cancer to be treated. In some cases, it may be necessary to provide a delayed release formulation to ensure that the active compound is not released until the formulation reaches the site where it is required. The formulations may additionally contain other ingredients and in tablets, one or more suitable carriers will generally be present. Typical carriers include lactose, saccharose, potato starch, calcium stearate and methylcellulose.

Injectable preparations may contain a solution of GMDP or GMDP-A or, alternatively, the compounds may be encapsulated in liposomes to form an injectable preparation.

Vaginal and rectal formulations may be formulated as pessaries and suppositories respectively. It is likely that these formulations will also contain other excipients and suitable carriers and excipients are well known to those skilled in the art of formulation.

Transdermal and other topical formulations may be in the form of ointments, creams or lotions and, again, suitable carriers and excipients are well known in the art.

Moreover, to improve permeation of compound into the skin, it may be preferable to employ particularly lipophilic analogues. Alternatively, skin-permeability modifying compounds may be present in the formulations, or electric potential may be employed to drive charged analogues into the skin. For transdermal formulations, the formulation may be incorporated into a transdermal patch or similar device.

Vaginal, rectal, topical and transdermal formulations are all new and themselves form a further aspect of the invention. In this aspect of the invention there is provided a composition comprising a muramyl peptide compound and a pharmaceutically acceptable excipient or carrier, characterised in that the composition is adapted for administration by the topical, transdermal, rectal or vaginal routes.

Topical and transdermal formulations are, as mentioned above, likely to be particularly useful in the prophylaxis of skin cancer and muramyl peptides may be included in topical sun screens as an additional protection against cancers of the skin.

The precise dosage for administration will be judged by the clinician or physician. However, in general, an average daily dose would be in the range of from 0.1 to 100 mg per day (or per tablet or other unit dose). It is likely that a dosage range of from 0.5 mg to 50 mg per day (or per tablet or other unit dose) will be preferred and a daily dosage of around 1.0 mg to 10 mg is considered to be optimal.

BRIEF DESCRIPTION OF THE FIGURES

The invention will now be further described by the following non-limiting examples and the following drawings in which.

EXAMPLES

Example 1

Figure 1:
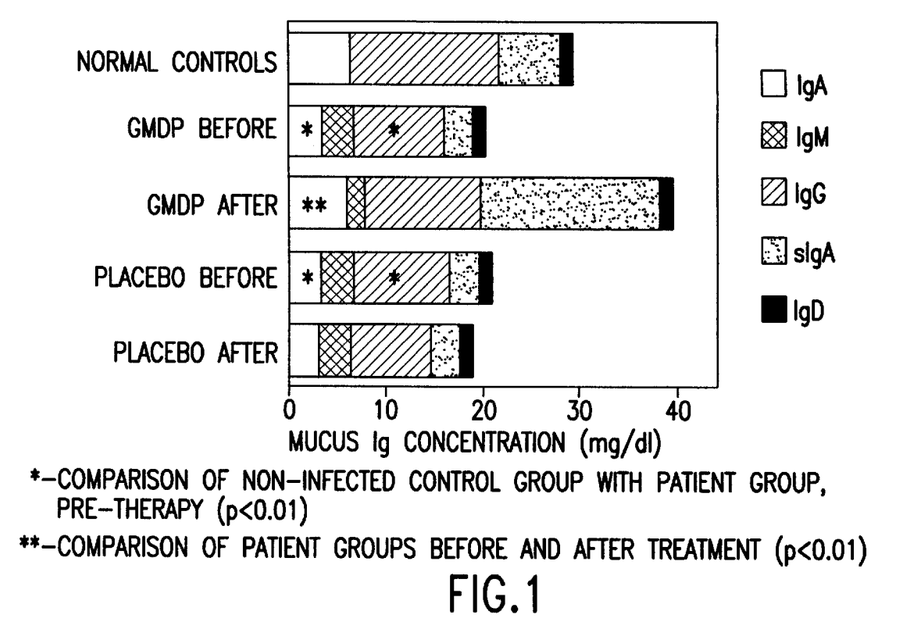
FIG. 1 is a histogram showing the effect of GMDP on Ig content of cervical mucus in patients with HPV infection of the uterine cervix.
Figure 2:
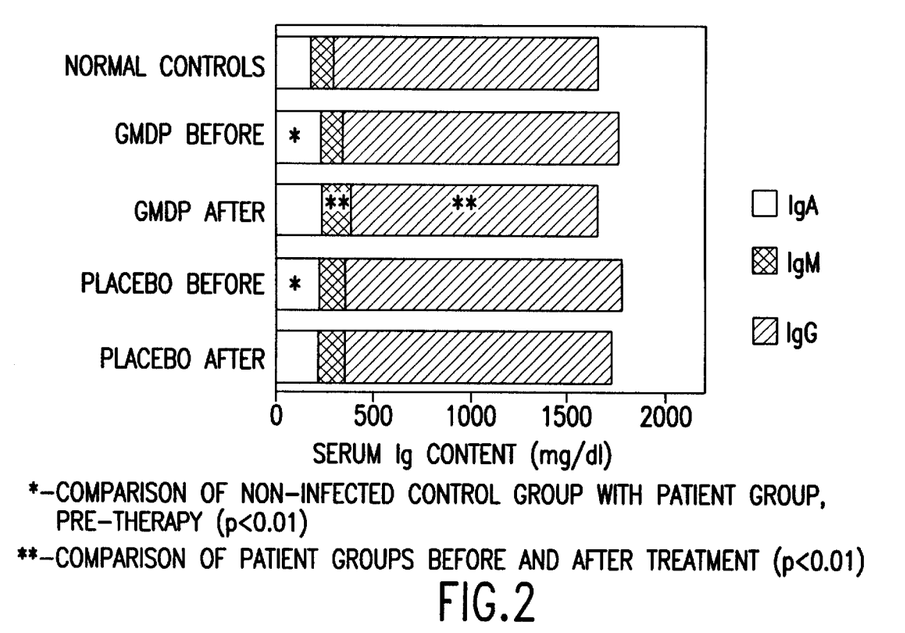
FIG. 2 is a histogram showing the effect of GMDP on serum Ig levels in patients with HPV infection of the uterine cervix.
Figure 3:
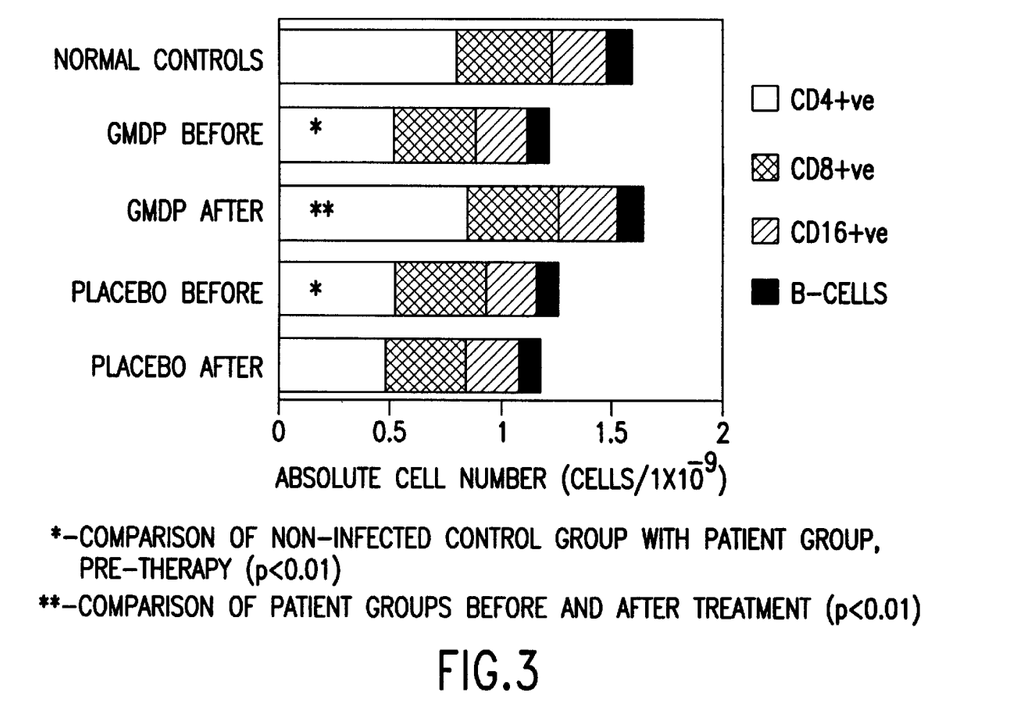
FIG. 3 is a histogram showing the effect of GMDP on lymphocyte sub-populations in patients with HPV infection of the uterine cervix.

The use of GMDP in the treatment of precancerous Human Papilloma Virus (HPV) infections of the uterine cervix.

Method:

The study group consisted of 50 women between 20 and 30 years of age (mean 26.7) with HPV of the cervix. The duration of the disease varied from 1 to 3.5 years. Thirty of the women received GMDP as part of a combined treatment, the other 20 received placebo in their combined therapy. To control for variation in Ig content of cervical secretions during the menstrual cycle, treatment was commenced 8–10 days after the beginning of the period.

A number of immunological parameters were monitored before the beginning of treatment; immunoglobulin (Ig) in serum (radial immunodiffusion), Ig in saliva and genital tract secretions (ELISA), subpopulations of immune cells (immunocytofluorimetry).

Subjects then received conventional treatment of antibiotics for accompanying bacterial infection; destruction of HPV infected cervical epithelium (condylomas) by laser and cryotherapy, and immunotherapy consisting of 1 mg of GMDP orally each day for ten days. Control subjects received placebo in place of GMDP.

Three days after the final GMDP (or placebo) administration, subjects underwent the same panel of immunological investigations. Follow up studies on the clinical progression of the HPV infection were performed Control values for immunological parameters were also taken from a group of women free of HPV infection. Their age range was 20 to 30 years with a mean of 25.6.

Results:

Clinical outcome:

During the follow up period the results of treatment were evaluated by colposcopy and cytological examination. As is shown in Table 1, an increase in the rate of cure was seen in the group of subjects that received GMDP as an adjunct to laser and cryotherapy.

TABLE 1

The effect of GMDP on cure and recurrence of HPV infection of the uterine cervix Treatment group Treatment Group

|  | GMDP | Placebo |
| --- | --- | --- |
| No. in group | 30 | 20 |
| Clinical Outcome |  |  |
| Full Cure | 27 (90%) | 13 65%) |
| Recurrence of HPV | 3 (10%) | 7 (35%) |

Immunological endpoints:

Normal controls showed a number of differences to patients before the treatment period (Table 2). Placebo treatment (laser or cryotherapy but no immunotherapy) did not produce any differences before and after treatment. However, in the GMDP group a number of significant treatment related changes were identified. Notably, the lower level of IgA and sIgA in cervical mucus was increased and in the latter case, came to exceed that found in normal controls.

A number of changes related to GMDP administration were also observed in the number of blood cells and the distribution of sub-types. Infected patients had a significantly lower leukocyte count compared to the non-infected controls. This was increased by GMDP treatment, but not in the placebo group. Total lymphocyte count was also increased by GMDP treatment, this being due mainly to increases in T-cells (CD3+ve), particularly the CD4+ve subset.

Conclusions:

The administration of GMDP to patients with HPV infection of the uterine cervix induced significant changes in a number of immunological parameters. These are probably related to the trend towards an increased cure rate associated with adjunct GMDP therapy.

TABLE 2

Immunoglobulin levels (mg/dl) in patients with HPV infection of the uterine cervix

|  | Non-infected Controls | GMDP Before | GMDP After | Placebo Before | Placebo After |
| --- | --- | --- | --- | --- | --- |
| Serum |  |  |  |  |  |
| IgA | 169.3 ± 11.0 | 216.0* ± 16.8 | 228.7 ± 18.2 | 221.0* ± 15.3 | 217.0 ± 20.0 |
| IgM | 112.7 ± 16.2 | 123.8 ± 10.4 | 160.8** ± 11.2 | 133.2 ± 12.1 | 129.8 ± 10.2 |
| IgG | 1375 ± 88 | 1424 ± 48 | 1258** ± 51 | 1442 ± 52 | 1386 ± 45 |
| Mucus of Uterine Cervix |  |  |  |  |  |
| IgA | 6.08± 0.86 | 3.15*± 1.08 | 5.96**± 1.05 | 3.28*± 0.68 | 3.08± 1.23 |
| IgM | 0 | 3.18 ± 2.21 | 1.8 ± 1.65 | 3.25 ± 2.01 | 3.31± 2.34 |
| IgG | 15.42± 1.32 | 9.57*± 2.19 | 12.01 ± 3.01 | 10.01*± 2.30 | 8.4 ± 3.05 |
| sIgA | 7.19± 0.62 | 3.80*± 0.84 | 19.4** ± 3.11 | 4.01*± 0.76 | 3.75± 0.81 |
| IgD | 0.26± 0.11 | 0.326± 0.16 | 0.315 ± 0.17 | 0.341± 0.19 | 0.29± 0.21 |
| Saliva |  |  |  |  |  |
| IgA | 3.07± 0.62 | 11.45*± 3.48 | 13.16 ± 2.98 | 10.89*± 3.91 | 10.1 ± 3.71 |
| IgM | 0 | 3.17 ± 1.05 | 1.65 ± 1.11 | 2.89 ± 1.49 | 3.07± 2.01 |
| IgG | 6.07± 0.79 | 16.19*± 4.01 | 15.05 ± 4.88 | 15.45 ± 4.3 | 13.02± 4.13 |
| sIgA | 12.4 ± 1.46 | 26.53*± 5.23 | 25.46 ± 4.96 | 24.3* ± 5.11 | 27.05± 6.12 |

*Comparison of non-infected control group with patient group, pre-therapy (p < 0.01)
**Comparison of patient groups before and after treatment (p < 0.01)

TABLE 3

Cell populations in blood of patients with HPV infection of the uterine cervix

|  | Non-infected Controls | GMDP Before | GMDP After | Placebo Before | Placebo After |
| --- | --- | --- | --- | --- | --- |
| Leukocytes |  |  |  |  |  |
| absolute | 5615 ± 200 | 4432* ± 310 | 5723** ± 304 | 4513* ± 270 | 4374 ± 265 |
| Lymphocytes |  |  |  |  |  |
| % | 35.4 ± 2.86 | 34.11± 3.16 | 35.77± 2.68 | 35.01± 2.73 | 34.80 ± 2.8 |
| absolute | 1988 ± 161 | 1511* ± 140 | 2046** ± 153 | 1579* ± 123 | 1521 ± 122 |

TABLE 3-continued

Cell populations in blood of patients with HPV infection of the uterine cervix

| | Non-infected Controls | GMDP Before | GMDP After | Placebo Before | Placebo After |
|---|---|---|---|---|---|
| CD3 +ve | | | | | |
| % | 60.4 ± 3.4 | 55.8 ± 4.1 | 59.12 ± 3.6 | 54.9 ± 3.81 | 55.1 ± 3.71 |
| absolute | 1201 ± 67.6 | 843.1* ± 61.9 | 1210** ± 73.7 | 886.8 ± 60.2 | 837.9 ± 56.4 |
| CD4 +ve | | | | | |
| % | 40.3 ± 3.2 | 34.6 ± 3.1 | 41.8 ± 3.8 | 33.7 ± 3.17 | 32.0 ± 2.97 |
| absolute | 801.2 ± 63.6 | 522.8* ± 46.8 | 855.2** ± 75.7 | 532.1* ± 50.1 | 486.6 ± 45.2 |
| CD8 +ve | | | | | |
| % | 21.8 ± 4.1 | 24.2 ± 2.87 | 20.3 ± 3.17 | 25.1 ± 3.08 | 23.8 ± 3.2 |
| absolute | 433.4 ± 81.6 | 365.7 ± 43.4 | 415.3 ± 64.9 | 402.8 ± 49.4 | 361.9 ± 48.7 |
| B-cells | | | | | |
| % | 5.14 ± 1.05 | 5.30 ± 0.8 | 5.08 ± 1.07 | 5.28 ± 0.96 | 5.4 ± 1.1 |
| absolute | 102.6 ± 20.8 | 80.1 ± 12.1 | 103.8 ± 21.7 | 82.26 ± 15.0 | 82.12 ± 16.7 |
| CD16 +ve | | | | | |
| % | 12.4 ± 2.2 | 16.3 ± 2.1 | 13.1 ± 2.3 | 15.6 ± 3.1 | 16.1 ± 2.87 |
| absolute | 246.5 ± 43.4 | 246.3 ± 31.7 | 268.1 ± 47.1 | 246.3 ± 48.9 | 244.8 ± 43.6 |

*Comparison of non-infected control group with patient group, pre-therapy ($p < 0.01$)
**Comparison of patient groups before and after treatment ($p < 0.01$)

I claim:

1. A method for the treatment of a precancerous lesion leading to a mucosal or epithelal cancer, comprising administering to a patient suffiering from said precancerous lesion an effective amount of a muramyl peptide compound of low intrnsic pyrogenicity.

2. A method for the prophylaxis of a skin cancer, comprising administering to a patient an effective amount of a muramyl peptide compound.

3. The method of claims 1 or 2, wherein said cancer is cervical cancer, colorectal cancer, cancer of the anus, basal or squamous cell carcinoma, melanoma, penile squamous carcinoma, cancer of the penis, cancer of the vulva, cancer of the oral mucosa, gastric cancer, bladder carcinoma, or oesophageal squamous cell carcinoma.

4. The method of claim 1 or claim 2, wherein said muramyl peptide compound is administered in combination with surgery, chemotherapy, immunotherapy or radiation therapy.

5. The method of claim 1 or 2, wherein said muramyl peptide compound is N-acetylmuramyl-L-threonyl-D-isoglutamine (Thr-MDP) or N-acetylmuramyl-L-alanyl-D-glutamine n-butyl ester (Murabutide).

6. The method of claim 1 or claim 2, wherein the muramyl peptide compound is a compound of general formula II:

$$\left[ \begin{array}{c} \text{HOCH}_2 \\ \text{structure with HOCH}_2, \text{OH, NHAc, H}_3\text{CCHCOR} \end{array} \right]_n \quad \text{II}$$

wherein:
R represents an amino acid residue or a linear peptide built of from 2 to 6 amio acid residues, at least onae of the residues being optionally substituted with a lipophilic group; and
n is 1 or b 2;
or an anomer thereof.

7. The method of claim 6, wherein n is 1.

8. The method of claim 6, wherein the amiino acid residue is a residue of an L-ainio acid.

9. The method of claim 8, wherein the amino acid residue is a residue of L-alanie.

10. The method of claim 6, wherein the second amino acid residue in said linear peptide, if present, is of the D-configuration.

11. The method of claim 10, wherein said second amino acid residue is a residue of D-glutamic or D-aspartic acid or a mono-, di- or mixed $C_1$–$C_{22}$ alkyl ester, amide or $C_1$–$C_4$ alkyl amide thereof.

12. The method of claim 11, wherein said mixed alkyl ester is a $C_1$–$C_6$ alkyl ester.

13. The method of claim 10, wherein the second omino acid residue is D-isoglutaminyl or D-glutamyl.

14. The method of claim 6, wherein the third amino acid residue in said linear peptide, if present, if present, is of the L-configuration.

15. The method of claim 14, wherein said third amino acid residue is L-alanyl or L-lysyl.

16. The method of claim 6, wherein said amino acid residue or linear peptide is substituted with a lipophilic group.

17. The method of claim 6, wherein said compound is N-acetyl-glucosaminyl-N-acetyl-muramyl-L-alanyl-D-isoglutainie (GMDP).

18. The method of claim 6, wherein the compound is:
N-acetyl-glucosaminyl-N-acetyl-muramyl-L-alanyl-D-glutamic acid (GMDP-A);
N-acetyl-D-glucosaminyl-($\beta$1–4)-N-acetylmuramyl-L-alanyl-D-glutamine n-butyl ester (GMDP-OBu);
N-[N$\alpha$-Acetyl-D-glucosaminyl-($\beta$1–4)-N-acetylmuramyl-L-alanyl-D-isoglutaminyl ]-N$^{\neq}$-stearoyl-L-lysine (GMDP-Lys(St));
N$^\alpha$[N-Acetyl-D-glucosaminyl-($\beta$1–4)-N-acetyl-muramyl-L-alanyl-$\gamma$-D-glutamyl ]-N$^{\neq}$-stearoyl-L-lysine (GMDPA-Lys(St));

N-Acetyl-D-glucosaminyl-($\beta$1–4)-N-acetylmuramyl-L-alanyl-D-glutamic acid dibenzyl ester (GMDPA(OBzi)$_2$);

N-Acetyl-D-glucosaminyl-($\beta$1–4)-N-acetylmuramyl-N-methyl-L-alanyl-D-isoglutamine (Me-GMDP);

N-Acetyl-D-glucosaminyl-($\beta$1–4)-N-acetylmuramyl-($\beta$1–4)-N-acetyl-D-glucosaminyl-($\beta$1–4)-N-acetylmuramyl-bis-(L-alanyl-D-isoglutamine) ((GMDP)$_2$);

N-Acetyl-D-glucosaminyl-($\beta$1–4)-N-acetylmuramyl-($\beta$1–4)-N-acetyl-D-glucosaminyl-($\beta$1–4)-N-acetylmuramyl-bis-(L-alanyl-D-glutamic acid) ((GMDPA)$_2$);

N-Acetyl-D-glucosaminyl-($\beta$1–4)-N-acetylmuramyl-($\beta$1–4)-N-acetyl-D-glucosaminyl-($\beta$1–4)-N-acetylmuramyl-bis-(L-alanyl-D-isoglutaminyl-L-lysine) ((GMDP Lys)$_2$);

N-acetyl-D-glucosaminyl-($\beta$1–4)-N-acetylmuramyl-($\beta$1–4)-N-acetyl-D-glucosaminyl-($\beta$1–4)-N-acetylmuramyl-bis-[L-alanyl-D-isoglutaminyl-N$^{\neq}$-stearoyl-L-lysine] ([GMDP-Lys(St)]$_2$);

N-Acetyl-D-glucosaminyl-($\beta$1–4)-N-acetylmuramyl-L-alanyl-D-isoglutamine 1-adamantyl ester (GMDP-Ad);

L-Threonyl-N$^{\neq}$-[N-Acetyl-D-glucosaminyl-($\beta$1–4)-N-acetyl-muramyl-L-alanyl-$\gamma$-D-isoglutaminyl]-L-lysyl-L-prolyl-L-arginine (GMDP-tuftsin E);

N-Acetyl-D-glucosaminyl-($\beta$1–4)-N-acetyl-muramyl-L-alanyl-$\gamma$-D-isoglutaminyl-L-threonyl-L-lysyl-L-prolyl-L-arginine (GMDP-tuftsin A);

N-Acetyl-D-glucosaminyl-($\beta$1–4)-N-acetylmuramyl-L-alanyl-$\alpha$-D-glutamyl-L-lysyl-L-threonyl-N$^{\neq}$-stearoyl-L-lysyl-L-prolyl-L-arginine (GMDPA-tuftsin lipophilic);

N$^{\neq}$-[N-Acetyl-D-glucosaminyl-($\beta$1–4)-N-acetyl-muramyl-L-alanyl-$\gamma$-D-isoglutaminyl]-L-lysyl-L-histidyl-L-glycine amide (GMDPA-bursin);

N-Acetyl-D-glucosaminyl-($\beta$1–4)-N-acetylmuramyl-L-alanyl-D-isoglutaminyl-L-glutamyl-L-tryptophan (GMDP-thymogen I);

N-Acetyl-D-glucosaminyl-($\beta$1–4)-N-acetylmuramyl-L-alanyl-D-isoglutaminyl-$\epsilon$-aminohexanoyl-L-glutamyl-L-tryptophan (GMDP-thymogen II);

or N$^{60}$-[N-acetyl-D-glucosaminyl-($\beta$1–4)-N-acetyl-muramyl-L-alanyl-D-isoglutaninyl]-N$^{\epsilon}$-stearoyl-L-lysyl-L-glutamyl-L-tryptophan (GMDP-thymogen III).

19. The method of claim 1 or claim 2, wherein the muramyl peptide compound is administered via the oral, vaginal, rectal, topical, transdermal or parenteral route.

* * * * *

UNITED STATES PATENT AND TRADEMARK OFFICE
CERTIFICATE OF CORRECTION

PATENT NO. : 5,877,147
DATED : March 2, 1999
INVENTOR(S) : Pinegin, B.V.

It is certified that error appears in the above-identified patent and that said Letters Patent is hereby corrected as shown below:

Column 15, line 15, after "GMDP-thymogen III", please insert --N-acetylmuramyl-L-threonyl-D-isoglutamine which has the structure:--.

In Claim 1, column 21, line 54, please delete "treatnent' and insert therein --treatment--.

In Claim 1, column 21, line 55, please delete "epithelal" and insert therein --epithelial--.

In Claim 1, column 21, line 56, please delete "suffiering" and insert therein --suffering--.

In Claim 1, column 21, line 58, please delete "intrnsic" and insert therein --intrinsic--.

In Claim 6, column 22, line 25, please delete "amio" and insert therein --amino--.

In Claim 6, column 22, line 25, please delete "onae" and insert therein --one--.

In Claim 6, column 22, line 28, please delete "b".

In Claim 8, column 22, line 31, please delete "amiino" and insert therein --amino--.

In Claim 8, column 22, line 32, please delete "L-ainio" and insert therein --L-amino--.

In Claim 9, column 22, line 34, please delete "L-alanie" and insert therein --L-alanine--.

In Claim 13, column 22, line 44, please delete "omino" and insert therein --amino--.

In Claim 14, column 22, line 47, please delete "if present".

UNITED STATES PATENT AND TRADEMARK OFFICE
CERTIFICATE OF CORRECTION

PATENT NO. : 5,877,147
DATED : March 2, 1999
INVENTOR(S) : Pinegin, B.V.

It is certified that error appears in the above-identified patent and that said Letters Patent is hereby corrected as shown below:

In Claim 17, column 22, line 56, please delete "isoglutainie" and insert therein -- isoglutamine--.

In Claim 18, column 22, line 63, please delete "N$^*$" and insert therein --N$^\epsilon$--.

In Claim 18, column 22, line 66, please delete "N$^*$" and insert therein --N$^\epsilon$--.

In Claim 18, column 23, line 2, please delete "(GMDPA(OBzi)" and insert therein -- (GMDPA(OBzl)$_2$);--.

In Claim 18, column 23, line 3, please delete "$_2$);".

In Claim 18, column 23, line 21, please delete "N$^*$" and insert therein --N$^\epsilon$--.

In Claim 18, column 23, line 25, please delete "N$^*$" and insert therein --N$^\epsilon$--.

In Claim 18, column 24, line 6, please delete "N$^*$" and insert therein --N$^\epsilon$--.

UNITED STATES PATENT AND TRADEMARK OFFICE
CERTIFICATE OF CORRECTION

PATENT NO. : 5,877,147
DATED : March 2, 1999
INVENTOR(S) : Pinegin, B.V.

It is certified that error appears in the above-identified patent and that said Letters Patent is hereby corrected as shown below:

In Claim 18, column 24, line 9, please delete "$N^*$" and insert therein --$N^\epsilon$--.

In Claim 18, column 24, line 20, please delete "$N^{60}$" and insert therein --$N^\alpha$--.

In Claim 18, column 24, line 21, please delete "isoglutaninyl" and insert therein --isoglutaminyl--.

Signed and Sealed this

Eleventh Day of April, 2000

Q. TODD DICKINSON

*Attesting Officer*     *Director of Patents and Trademarks*